(12) United States Patent
Stinson et al.

(10) Patent No.: US 7,938,854 B2
(45) Date of Patent: *May 10, 2011

(54) MEDICAL DEVICES AND METHODS OF MAKING THE SAME

(75) Inventors: Jonathan S. Stinson, Minneapolis, MN (US); Barry O'Brien, Galway (IE); Steven E. Walak, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/784,134

(22) Filed: May 20, 2010

(65) Prior Publication Data

US 2010/0228336 A1    Sep. 9, 2010

Related U.S. Application Data

(62) Division of application No. 11/035,316, filed on Jan. 13, 2005, now Pat. No. 7,727,273.

(51) Int. Cl.
*A61F 2/06* (2006.01)
*A61F 2/82* (2006.01)
*C22C 27/02* (2006.01)

(52) U.S. Cl. ........................ 623/1.15; 420/426; 420/580

(58) Field of Classification Search .................. None
See application file for complete search history.

(56) References Cited

U.S. PATENT DOCUMENTS

| | | | |
|---|---|---|---|
| 2,907,654 A | 10/1959 | Thielemann | |
| 3,128,178 A | 4/1964 | Duffek, Jr. | |
| 3,140,943 A | 7/1964 | Field et al. | |
| 3,186,837 A | 6/1965 | Duffek, Jr. | |
| 3,188,205 A * | 6/1965 | Michael | 420/426 |
| 3,230,119 A * | 1/1966 | Gemmell et al. | 148/668 |
| 3,346,380 A | 10/1967 | Amra | |
| 3,540,863 A * | 11/1970 | Priceman et al. | 428/641 |
| 3,549,429 A * | 12/1970 | Rausch et al. | 428/610 |
| 3,573,902 A | 4/1971 | Delgrosso | |
| 3,667,940 A * | 6/1972 | McDonald | 420/426 |
| 3,679,494 A | 7/1972 | Hill et al. | |
| 4,526,749 A | 7/1985 | Huber, Jr. et al. | |
| 4,655,771 A | 4/1987 | Wallsten | |
| 4,800,882 A | 1/1989 | Gianturco | |
| 4,856,516 A | 8/1989 | Hillstead | |
| 4,958,625 A | 9/1990 | Bates et al. | |

(Continued)

FOREIGN PATENT DOCUMENTS

EP    1 403 390    9/2003

(Continued)

OTHER PUBLICATIONS

The Physics of Radiology, HE Johns, JR Cunningham, Charles C Thomas Publisher, 1983, pp. 133-143.

(Continued)

*Primary Examiner* — John J Zimmerman

(74) *Attorney, Agent, or Firm* — Fish & Richardson P.C.

(57) ABSTRACT

Medical devices, such as stents, and methods of making the devices are disclosed. In some embodiments, a medical device includes an alloy having tantalum, tungsten, zirconium and niobium. For example, the alloy can include from about 20% to about 40% by weight of tantalum, from about 0.5% to about 9% by weight of tungsten, and from about 0.5% to about 10% by weight of zirconium.

20 Claims, 1 Drawing Sheet

U.S. PATENT DOCUMENTS

| | | | |
|---|---|---|---|
| 5,090,419 A | 2/1992 | Palestrant | |
| 5,195,969 A | 3/1993 | Wang et al. | |
| 5,270,086 A | 12/1993 | Hamlin | |
| 5,366,504 A | 11/1994 | Andersen et al. | |
| 5,368,045 A | 11/1994 | Clement et al. | |
| 5,380,375 A | 1/1995 | Hashimoto et al. | |
| 5,628,787 A | 5/1997 | Mayer | |
| 5,630,840 A | 5/1997 | Mayer | |
| 5,636,641 A | 6/1997 | Fariabi | |
| 5,674,242 A | 10/1997 | Phan et al. | |
| 5,679,470 A | 10/1997 | Mayer | |
| 5,690,670 A | 11/1997 | Davidson | |
| 5,725,570 A | 3/1998 | Heath | |
| 5,728,158 A | 3/1998 | Lau et al. | |
| 5,780,807 A | 7/1998 | Saunders | |
| 5,800,511 A | 9/1998 | Mayer | |
| 5,800,519 A | 9/1998 | Sandock | |
| 5,824,077 A | 10/1998 | Mayer | |
| 6,146,404 A | 11/2000 | Kim et al. | |
| 6,171,327 B1 | 1/2001 | Daniel et al. | |
| 6,245,104 B1 | 6/2001 | Alt | |
| 6,264,595 B1 | 7/2001 | Delfino et al. | |
| 6,287,331 B1 | 9/2001 | Heath | |
| 6,290,721 B1 | 9/2001 | Heath | |
| 6,340,367 B1 | 1/2002 | Stinson et al. | |
| 6,342,062 B1 | 1/2002 | Suon et al. | |
| 6,379,383 B1 | 4/2002 | Palmaz et al. | |
| 6,387,121 B1 | 5/2002 | Alt | |
| 6,440,487 B1 | 8/2002 | Delfino et al. | |
| 6,478,815 B1 | 11/2002 | Alt | |
| 6,527,802 B1 | 3/2003 | Mayer | |
| 6,726,712 B1 | 4/2004 | Raeder-Devens et al. | |
| 7,041,127 B2 | 5/2006 | Ledergerber | |
| 7,101,391 B2 | 9/2006 | Scheuermann et al. | |
| 7,101,392 B2 | 9/2006 | Heath | |
| 7,244,319 B2 | 7/2007 | Abrams et al. | |
| 7,250,058 B1 | 7/2007 | Pacetti et al. | |
| 7,318,837 B2 | 1/2008 | Krivoruchko et al. | |
| 7,335,227 B2 | 2/2008 | Jalisi | |
| 7,344,560 B2 * | 3/2008 | Gregorich et al. | 623/1.15 |
| 7,727,273 B2 * | 6/2010 | Stinson et al. | 623/1.15 |
| 2002/0095207 A1 | 7/2002 | Moriuchi et al. | |
| 2002/0111694 A1 | 8/2002 | Ellingsen et al. | |
| 2002/0144757 A1 | 10/2002 | Craig et al. | |
| 2003/0003220 A1 | 1/2003 | Zhong et al. | |
| 2003/0009215 A1 | 1/2003 | Mayer | |
| 2003/0018380 A1 | 1/2003 | Craig et al. | |
| 2003/0050691 A1 | 3/2003 | Shifrin et al. | |
| 2003/0077200 A1 | 4/2003 | Craig et al. | |
| 2003/0088308 A1 | 5/2003 | Scheuermann et al. | |
| 2003/0181972 A1 | 9/2003 | Jansen et al. | |
| 2003/0185895 A1 | 10/2003 | Lanphere et al. | |
| 2004/0044397 A1 | 3/2004 | Stinson | |
| 2004/0062676 A1 | 4/2004 | Trotzschel et al. | |
| 2004/0143317 A1 | 7/2004 | Stinson et al. | |
| 2004/0158309 A1 * | 8/2004 | Wachter et al. | 623/1.13 |
| 2004/0182199 A1 * | 9/2004 | Naito | 75/245 |
| 2006/0079953 A1 | 4/2006 | Gregorich et al. | |
| 2006/0153729 A1 | 7/2006 | Stinson et al. | |
| 2007/0233217 A1 | 10/2007 | Yang et al. | |
| 2007/0233231 A1 | 10/2007 | Krivoruchko et al. | |
| 2008/0109068 A1 | 5/2008 | Fischell et al. | |
| 2008/0195194 A1 | 8/2008 | Pacetti et al. | |
| 2009/0227902 A1 | 9/2009 | Simpson et al. | |

FOREIGN PATENT DOCUMENTS

| | | |
|---|---|---|
| EP | 1 444 993 | 8/2004 |
| GB | 933 712 | 8/1963 |
| WO | WO 85/04802 | * 11/1985 |
| WO | WO 94/16646 | 8/1994 |
| WO | WO 95/30384 | 11/1995 |
| WO | WO 99/39660 | 8/1999 |
| WO | WO 02/05863 | 1/2002 |
| WO | WO 02/38080 | 5/2002 |
| WO | WO 02/43787 | 6/2002 |
| WO | WO 2004/019822 | 3/2004 |
| WO | WO 2004/022122 | 3/2004 |
| WO | WO 2006/076447 | 7/2006 |

OTHER PUBLICATIONS

Schetsky, Shape Memory Alloys, Encyclopedia of Chemical technology ($3^{rd}$ edition) John Wiley & Sons, 1982, pp. 726-736.

Poncin et al., "Comparing and Optimizing Co-Cr Tubing for Stent Applications," *Materials & Processes for Medical Devices Conference*, Aug. 25-27, 2004, 6 pages.

DiStefano et al., "Oxidation and its effects on the mechanical properties of Nb-1Zr," *J. Nucl. Mater.*, 2001, 295:42-48.

* cited by examiner

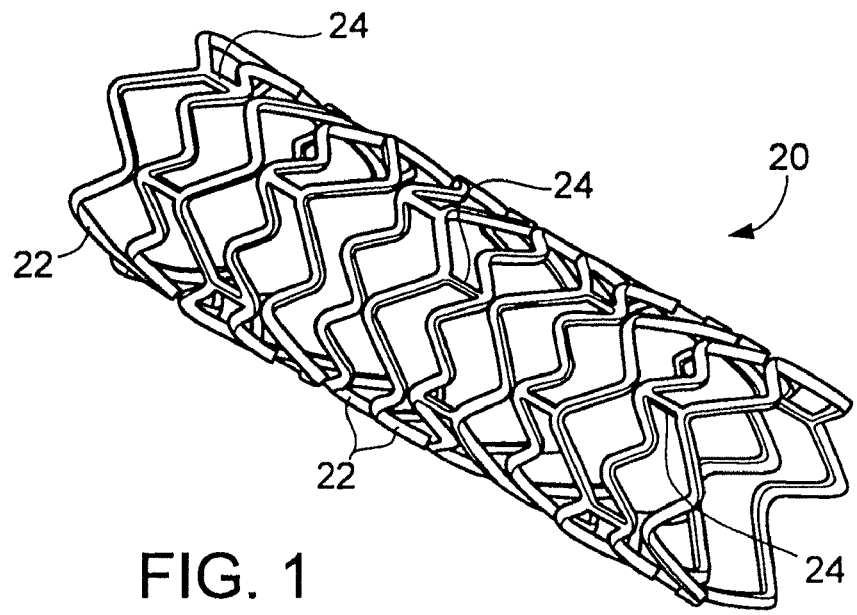
FIG. 1
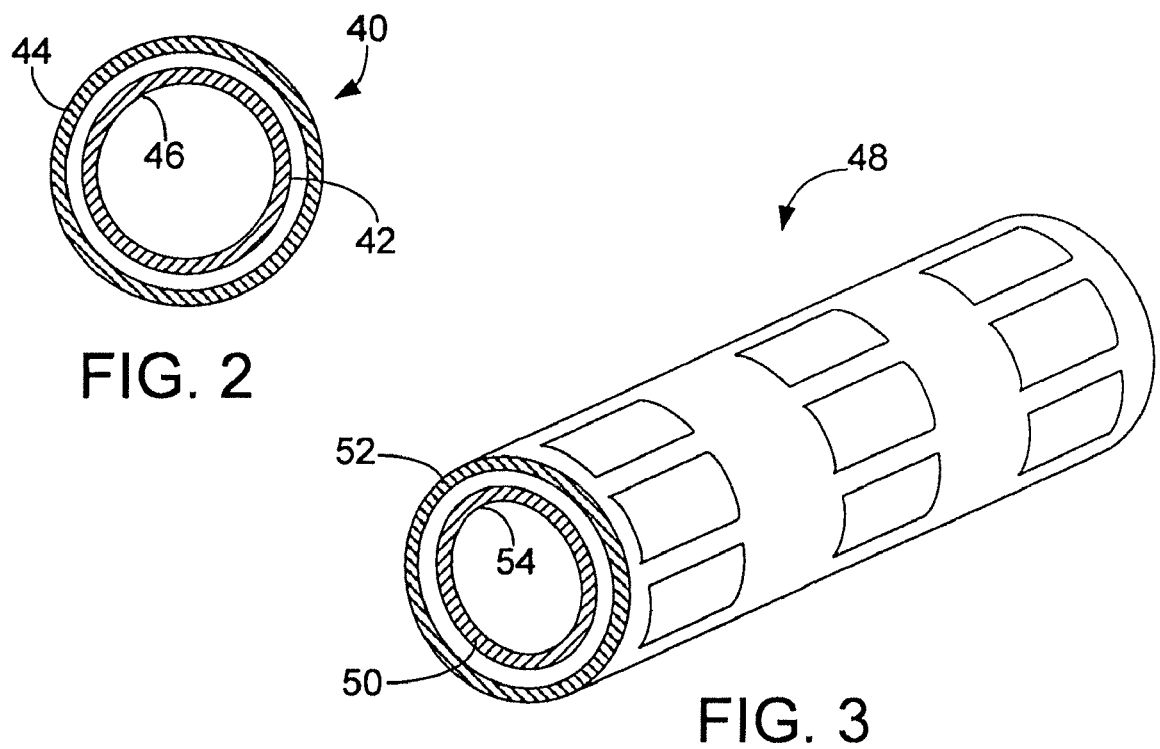
FIG. 2
FIG. 3

MEDICAL DEVICES AND METHODS OF MAKING THE SAME

CROSS-REFERENCE TO RELATED APPLICATIONS

This application is a divisional application of and claims priority to U.S. application Ser. No. 11/035,316, filed on Jan. 13, 2005, now U.S. Pat. No. 7,727,273. The above noted application is hereby incorporated by reference in its entirety.

TECHNICAL FIELD

The invention relates to medical devices, such as stents, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents, stent-grafts, and covered stents.

An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

When the endoprosthesis is advanced through the body, its progress can be monitored, e.g., tracked, so that the endoprosthesis can be delivered properly to a target site. After the endoprosthesis is delivered to the target site, the endoprosthesis can be monitored to determine whether it has been placed properly and/or is functioning properly. Methods of tracking and monitoring a medical device include X-ray fluoroscopy and magnetic resonance imaging (MRI).

SUMMARY

The invention relates to medical devices, such as stents, and methods of making the medical devices.

In one aspect, the invention features a medical device including an alloy having tantalum, niobium, tungsten and zirconium. The alloy has a balance of physical properties and mechanical properties that make it well suited for medical device applications. For example, the alloy has low magnetic susceptibility so as to have reduced image voids or distortions during magnetic resonance imaging, and a good balance of radiopacity (e.g., not too bright in radiography images so as to obscure visibility of stented lumen features while using computed tomography (CT) or fluoroscopy imaging). As a result, magnetic resonance imaging, radiographic diagnostic imaging and angiography can be performed with a medical device including the alloy. At the same time, the alloy has mechanical properties, such as yield strength, ultimate tensile strength, ductility, stiffness, fatigue strength and toughness, that allow it to be processed and formed into a medical device, and to be used as a medical device. The alloy may also exhibit corrosion resistance and biocompatibility that are useful for many medical device applications.

Embodiments may include one or more of the following features. The alloy includes from about 20% to about 40% by weight of tantalum. The alloy includes from about 0.5% to about 9% by weight of tungsten. The alloy includes from about 0.5% to about 10% by weight of zirconium. The alloy includes from about 41% to about 79% by weight of niobium. The alloy includes from about 20% to about 40% by weight of tantalum, from about 0.5% to about 9% by weight of tungsten, and from about 0.5% to about 10% by weight of zirconium. The alloy further includes a balance of niobium. The alloy includes from about 1% to about 19% by weight of tungsten and/or zirconium. The alloy further includes an element selected from the group consisting of molybdenum, rhenium, iridium, and hafnium.

The alloy may have one or more of the following properties. The alloy may have a Young's (elastic) modulus of from about 10 million psi to about 30 million psi. The alloy may have a yield strength of from about 20 thousand to about 60 thousand psi. The alloy may have a percent elongation of from about 10% to about 40% to fracture.

The medical device may further include a filament having at least a portion including the alloy.

The medical device may further include a tubular member including the alloy.

The medical device may further include a multilayered structure, wherein at least one layer includes the alloy. The multilayered structure may be in the form of a tubular member or a filament.

The medical device can be constructed in a variety of forms. The medical device can be adapted to be implanted in a body, for example, by being in the form of a stent. The medical device can be in the form of a needle, a catheter, a guidewire, an orthopedic implant, an intraluminal filter, or a dental prosthesis. The medical device can be in the form of forceps, clamps, or fixtures.

In another aspect, the invention features a medical device including an alloy consisting or consisting essentially of tantalum, tungsten, zirconium and niobium.

Embodiments may include one or more of the following features.

In another aspect, the invention features a method of making a medical device. The method includes forming an alloy as described herein, and using the alloy to form the medical device, wholly or in part.

In another aspect, the invention features an alloy composition as described herein.

As used herein, an alloy is a homogeneous substance including two or more metals or a metal and nonmetal intimately united, such as by being fused together or dissolving in each other when molten, and remaining fused together or dissolved in each other when solid.

The concentrations described herein are expressed in weight percents.

Other aspects, features, and advantages will be apparent from the description of the preferred embodiments thereof and from the claims.

DESCRIPTION OF DRAWINGS

FIG. 1 is a perspective view of an embodiment of a stent.
FIG. 2 is a cross-sectional view of an embodiment of a multilayered wire.
FIG. 3 is a perspective view of an embodiment of a multilayered tube.

DETAILED DESCRIPTION

Referring to FIG. 1, a stent 20 has the form of a tubular member defined by a plurality of bands 22 and a plurality of connectors 24 that extend between and connect adjacent bands. During use, bands 22 are expanded from an initial, small diameter to a larger diameter to contact stent 20 against a wall of a vessel, thereby maintaining the patency of the vessel. Connectors 24 provide stent 20 with flexibility and conformability so that the stent can adapt to the contours of the vessel.

Stent 20 includes (e.g., is formed of) a biocompatible alloy composition that is capable of providing stent 20 with a balance of physical properties and mechanical properties that enhances the performance of the stent. For example, the alloy composition includes relatively dense elements, such as tantalum and tungsten, that enhance the radiopacity of stent 20; as a result, the stent can be easily detected during X-ray fluoroscopy and CT. The alloy composition also includes elements, such as niobium, that have low magnetic susceptibility; as a result, stent 20 can be compatible with MRI techniques, e.g., by not producing substantial amounts of magnetic artifacts, image distortions or voids, and/or by not heating or moving during imaging.

At the same time, as described below, the alloy composition has mechanical properties that allow it to be processed and formed into a medical device, and to provide the device with good mechanical performance. For example, the alloy composition has a strength and ductility such that it can be cold worked to form a tube from which stent 20 can be formed. The alloy composition can also have a stiffness or elastic modulus to provide stent 20 with reduced recoil, e.g., when the stent is crimped on a delivery catheter or when the stent is expanded against a vessel wall.

The alloy composition includes an intimate combination (e.g., a solid solution) of tantalum, tungsten, zirconium, and niobium. Niobium, which is a low magnetic susceptibility material, makes up the greatest portion of the alloy composition. The other elements, which have good solubility in niobium, are believed to further contribute to the mechanical and/or physical properties of the alloy composition, without substantially and adversely affecting the magnetic susceptibility of the composition. In some embodiments, the alloy composition further includes molybdenum, rhenium, iridium, and/or hafnium, in any combination.

Tungsten and zirconium are capable of strengthening the alloy composition, e.g., by solid solution strengthening. In addition, tungsten is also capable of enhancing the radiopacity of the alloy composition. The concentrations of the tungsten and zirconium are selected to provide one or more targeted mechanical properties (described below). In some embodiments, the alloy composition includes from about 0.1% to about 25% by weight of tungsten and zirconium, in any ratio. For example, of the total amount of tungsten and zirconium in the alloy composition, the alloy composition can include greater than or equal to about 0%, about 10%, about 20%, about 30%, about 40%, about 50%, about 60%, about 70%, about 80%, or about 90% of tungsten, with the remainder being zirconium; and/or less than or equal to about 100%, about 90%, about 80%, about 70%, about 60%, about 50%, about 40%, about 30%, about 20%, or about 10% of tungsten, with the remainder being zirconium. The alloy composition can include greater than or equal to about 0.1%, about 1%, about 3%, about 5%, about 7%, about 9%, about 11%, about 13%, about 15%, about 17%, about 19%, about 21%, or about 23% by weight of tungsten and/or zirconium; and/or less than or equal to about 25%, about 23%, about 21%, about 19%, about 17%, about 15%, about 13%, about 11%, about 9%, about 7%, about 5%, about 3%, or about 1% by weight of tungsten and/or zirconium. In some embodiments, the alloy composition can include from about 0.1% to about 15% by weight of tungsten, and from about 0.1% to about 10% by weight of zirconium. The concentration of tungsten can be greater than or equal to about 0.1%, about 1%, about 3%, about 5%, about 7%, about 9%, about 11%, or about 13% by weight; and/or less than or equal to about 15%, about 13%, about 11%, about 9%, about 7%, about 5%, about 3%, or about 1% by weight. The concentration of zirconium can be greater than or equal to about 0.1%, about 2%, about 4%, about 6%, or about 8% by weight; and/or less than or equal to about 10%, about 8%, about 6%, about 4%, or about 2% by weight.

Tantalum is capable of increasing the radiopacity of the alloy composition and strengthening the composition, albeit less so than tungsten and zirconium. Tantalum can also enhance the ductility of the alloy composition so that the composition can be conveniently worked. The concentration of tantalum in the alloy composition can be from about 0.1% to about 40% by weight. For example, the concentration of tantalum can be greater than or equal to about 0.1%, about 2%, about 4%, about 6%, about 8%, about 10%, about 12%, about 14%, about 16%, about 18%, about 20%, about 22%, about 24%, about 26%, about 28%, about 30%, about 32%, about 34%, about 36%, or about 38% by weight; and/or less than or equal to about 40%, about 38%, about 36%, about 34%, about 32%, about 30%, about 28%, about 26%, about 24%, about 22%, about 20%, about 18%, about 16%, about 14%, about 12%, about 10%, about 8%, about 6%, about 4%, or about 2% by weight.

In some embodiments, the alloy composition further includes one or more (e.g., two, three or four) elements selected from the group consisting of molybdenum, rhenium, iridium, and hafnium. These elements have atomic sizes and solubility characteristics that allow them to form a solid solution with niobium. These elements can also enhance the mechanical properties of the alloy composition, e.g., by increasing the elastic modulus. These elements can be incorporated into the alloy composition to replace a portion of or all of the tantalum, zirconium, and/or tungsten, in any combination.

Rhenium and molybdenum are highly potent strengtheners and may be added to the alloy to increase the yield strength and ultimate tensile strength by solid solution strengthening. In some embodiments, the alloy includes from about 0.5% to about 5% by weight of rhenium and/or molybdenum. The alloy may include greater than or equal to about 0.5%, about 1%, about 2%, about 3%, or about 4% by weight of rhenium and/or molybdenum; and/or less than or equal to about 5%, about 4%, about 3%, about 2%, or about 1% by weight of rhenium and/or molybdenum. Of the total amount of rhenium and molybdenum in the alloy, rhenium can be present from about 0% to 100%, with the remainder being molybdenum, similar to that described above for tungsten and zirconium. In embodiments including rhenium and/or molybdenum, the tantalum concentration is as described above to enhance elastic modulus and radiopacity. The niobium concentration can be reduced to compensate for the rhenium and molybdenum additions, and the concentrations of tungsten and zirconium can be as described above or reduced to about one-half of their concentrations in an alloy that does not contain rhenium and/or molybdenum. For example, if there were about 3.5% tungsten and about 1.3% zirconium in an alloy that does not contain Re and Mo, then there may be about 1.8% tungsten and about 0.6% zirconium in an alloy that includes Re and Mo additions.

Iridium, which has an elastic modulus of about 76 million psi, can be added to the alloy to increase the modulus (stiffness) of the alloy, and to enhance hot workability and ductility. Iridium is soluble in tantalum (e.g., up to about 5%) and niobium (e.g., up to about 12%). In some embodiments, iridium is added to up to 5% of the tantalum concentration in the alloy. In other embodiments, the alloy includes from about 0.5% to about 8% by weight of iridium. For example, the iridium concentration can be greater than or equal to about 0.5%, about 1%, about 2%, about 3%, about 4%, about 5%, about 6%, or about 7% by weight; and/or less than or equal to about 8%, about 7%, about 6%, about 5%, about 4%, about 3%, about 2%, or about 1% by weight.

Hafnium may be added to enhance the hot workability, ductility and stiffness of the alloy. Hafnium can act as a grain boundary strengthener at elevated temperatures, and as a result, the alloy may be less likely to tear at the grain boundaries during hot working operations. For example, hafnium may react with trace carbon in the starting materials to form hafnium carbides in the matrix of the alloy so that the carbon does not react with niobium and/or tantalum to form excessive amounts of niobium carbides and/or tantalum carbides along grain boundaries. The carbides in the grain boundaries can reduce grain boundary ductility and increase the alloy susceptibility to intergranular failure. Hafnium, which is soluble to about 18% by weight in niobium and to 5% in tantalum, can be added in the range of about 1% to about 12%. For example, the hafnium concentration can be greater than or equal to about 1%, about 3%, about 5%, about 7%, about 9%, or about 11% by weight; and/or less than or equal to about 12%, about 10%, about 8%, about 6%, about 4%, or about 2% by weight. In some embodiments, hafnium is added up to 5% of the tantalum concentration.

Titanium, which is well soluble in niobium and tantalum but has a relatively low elastic modulus, may be added to enhance the stiffness, hot workability and ductility of niobium. In particular, since some of the other elements that may be present in the alloy serve to increase the strength of the alloy, titanium may be added to provide a balance between strength and ductility. In some embodiments, titanium is present in the range of from about 0.5% to about 20%, such as from about 1% to about 10%, by weight. For example, the titanium concentration can be greater than or equal to about 0.5%, about 2%, about 4%, about 6%, about 8%, about 10%, about 12%, about 14%, about 16%, or about 18% by weight; and/or less than or equal to about 20%, about 18%, about 16%, about 14%, about 12%, about 10%, about 8%, about 6%, about 4%, or about 2% by weight.

Niobium makes up the balance of the alloy composition, e.g., after accounting for the other elements in the alloy described above. In certain embodiments, the alloy composition includes from about 41% to about 79% by weight of niobium. For example, the alloy composition can include greater than or equal to about 41%, about 45%, about 50%, about 55%, about 60%, about 65%, about 70%, or about 75% by weight of niobium; and/or less than or equal to about 79%, about 75%, about 70%, about 65%, about 60%, about 55%, about 50%, or about 45% by weight of niobium.

As indicated above, in addition to having the above amounts of elements, the alloy composition can also have certain mechanical and physical properties that enhance the performance of the medical device in which the alloy composition is incorporated. For example, to form an ingot of the alloy composition into a feedstock of raw material (such as a tube), the alloy composition may have certain tensile properties (e.g., yield strength and ductility) and grain structure (e.g., equiaxed) that allow it to be processed (e.g., cold worked). In some embodiments, the alloy composition has a percent elongation in a room temperature tensile test of from about 10% to about 40% to fracture. For example, the percent elongation can be greater than or equal to about 10%, about 15%, about 20%, about 25%, about 30%, or about 35%; and/or less than or equal to about 40%, about 35%, about 30%, about 25%, about 20%, or about 15%. The yield strength and elastic modulus of the alloy composition are targeted to reduce recoil, e.g., when stent 20 is crimped or expanded. In some embodiments, the Young's (elastic) modulus from a room temperature tensile test is from about 10 msi (million psi) to 30 msi. The elastic modulus can be greater than or equal to about 10 million psi, about 15 million psi, about 20 million psi, or about 25 million psi; and/or less than or equal to about 30 million psi, about 25 million psi, about 20 million psi, or about 15 million psi. In some embodiments, the yield strength is from about 20 ksi to about 60 ksi. For example, the yield strength can be greater than or equal to about 20 ksi (thousand psi), about 25 ksi, about 30 ksi, about 35 ksi, about 40 ksi, about 45 ksi, about 50 ksi, or about 55 ksi; and/or less than or equal to about 60 ksi, about 55 ksi, about 50 ksi, about 45 ksi, about 40 ksi, about 35 ksi, about 30 ksi, or about 25 ksi.

As examples, referring to Table 1, some mechanical properties of the alloys described herein are shown. The alloys have high yield strengths (e.g., comparable to 316L stainless steel), high moduli, and high elongation to allow cold forming.

TABLE 1

| Material: | Modulus (E), msi | 0.2% Offset Yield Strength, ksi | UTS, ksi | % elongation |
|---|---|---|---|---|
| Nb—28Ta—3.5W—1.3Zr | 19 | 51 | 69 | 17 |
| Nb—10Hf—1Ti—0.7Zr—0.5Ta—0.5W | 16 | 45 | 62 | 23 |

The physical properties of the alloy composition that relate to magnetic resonance and radiographic imaging include its magnetic susceptibility and radiopacity. For MRI compatibility and safety, the alloy is formulated to reduce signal distortion and movement within the body or nerve simulation, by controlling the magnetic susceptibility and solubility of the alloy constituents. In some embodiments, the magnetic susceptibility of the alloy is less than the magnetic susceptibility of austenitic stainless steel (such as 316L stainless steel), e.g. in the same order of magnitude as titanium (about $10^{-4}$).

For radiopacity, the alloy is formulated to a desired mass absorption coefficient. Radiopacity is proportional to mass absorption coefficient and thickness. Higher material mass absorption coefficient and/or thickness may increase the radiopacity of a medical device. The radiopacity of a device is preferably sufficient for viewing but not too bright. For example, in some cases, the radiopacity of stents made of pure tantalum may be too high because X-ray image artifact, such as a halo about the stent, is produced. In embodiments, the stent is readily visible by fluoroscopy and CT, but does not appear so bright that detail adjacent to or within the lumen of the medical device in the fluoroscopic image is obscured or distorted. In some embodiments, the alloy of the medical device has a radiopacity (brightness in an X-ray film image) of from about 1.10 to about 3.50 times (e.g., greater than or equal to about 1.1, about 1.5, about 2.0, about 2.5, or about 3.0 times; and/or less than or equal to about 3.5, about 3.0, about 2.5, about 2.0, or about 1.5 times) that of the same medical device made from 316L grade stainless steel, as measured by ASTM F640 (Standard Test Methods for Radiopacity of Plastics for Medical Use). Furthermore, as a result of the increased radiopacity provided by the alloy composition, the thickness of the medical device can be reduced, e.g., relative to 316L stainless steel. In embodiments in which the medical device includes a stent, thinner stent walls provide the stent with enhanced flexibility and reduced profile. Mass absorption coefficients and densities for Nb, Ta, W, Zr, Mo, Re, Ir, and Hf at 0.050 MeV are listed in the Table 2 below.

TABLE 2

| | Metal | | | | | | | |
|---|---|---|---|---|---|---|---|---|
| | Nb | Ta | W | Zr | Mo | Re | Ir | Hf |
| Mass absorption coefficient, $cm^2/g$ | 6.64 | 5.72 | 5.95 | 6.17 | 7.04 | 6.21 | 6.69 | 5.48 |
| Density, g/cc | 8.57 | 16.7 | 19.3 | 6.5 | 10.2 | 21.0 | 22.65 | 13.1 |

In embodiments, the mass absorption coefficient of the alloy is from about 5.00 $cm^2/g$ to about 7.00 $cm^2/g$ at 0.050 MeV. Mass absorption coefficient can be calculated from the results of radiopacity tests, as described in *The Physics of Radiology*, H. E. Johns, J. R. Cunningham, Charles C. Thomas Publisher, 1983, Springfield, Ill., pp. 133-143.

The alloys can be synthesized by intimately combining the components of the alloys. In some embodiments, samples of an alloy composition are made by melting charges of the components to form a homogeneous alloy. The targeted alloy composition can be formed by melting the elemental starting materials (such as chips, powders, balls, pellets, bars, wires, and/or rods) in the concentrations described above. Melting can be performed in an inert atmosphere (e.g., argon pressure), in a partial pressure (in argon at a pressure less than atmospheric) or under vacuum using vacuum induction melting (VIM), vacuum arc remelting (VAR), electron beam melting (EBM), plasma melting, vacuum or inert gas plasma deposition, hot isostatic pressing, and/or cold pressing and sintering. The raw samples (initial form of the alloy) can be in the form of an ingot, a compact, or a deposit. The raw sample can then be formed, for example, into a billet using metallurgical techniques, such as pressing, forging, drawing, rolling, and extruding. The billet can be drawn into tubing or rolled into a sheet for stock stent tubing production.

In some embodiments, the tube that makes up the tubular member of stent 20 can be formed using metallurgical techniques, such as thermomechanical processes. For example, a hollow metallic member (e.g., a rod or a bar) of the alloy composition can be drawn through a series of dies to plastically deform the member to a targeted size and shape. The plastic deformation strain can harden the member (and increases its yield strength) and elongates the grains along the longitudinal axis of the member. Other methods include ingot metallurgy, extrusion and bar rolling, seamless tube drawing, and mechanical, laser or chemical machining. The deformed member can be heat treated (e.g., annealed above the recrystallization temperature and/or hot isostatically pressed) to transform the elongated grain structure into an initial grain structure, e.g., one including equiaxed grains.

Next, bands 22 and connectors 24 of stent 20 are formed, for example, by machining the tube. Selected portions of the tube can be removed to form bands 22 and connectors 24 by laser or waterjet cutting, as described in U.S. Pat. No. 5,780, 807, hereby incorporated by reference in its entirety. In certain embodiments, during laser cutting, a liquid carrier, such as a solvent or an oil, is flowed through the lumen of the tube. The carrier can prevent dross formed on one portion of the tube from re-depositing on another portion, and/or reduce formation of recast material on the tube. Other methods of removing portions of the tube can be used, such as mechanical machining (e.g., micro-machining), electrical discharge machining (EDM), and photoetching (e.g., acid photoetching).

In some embodiments, after bands 22 and connectors 24 are formed, areas of the tube affected by the cutting operation above can be removed. For example, laser machining of bands 22 and connectors 24 can leave a surface layer of melted and resolidified material and/or oxidized metal that can adversely affect the mechanical properties and performance of stent 20. The affected areas can be removed mechanically (such as by grit blasting or honing) and/or chemically (such as by etching or electropolishing).

After the removal of areas of the tube affected by the cutting operation, the unfinished stent is finished. The unfinished stent can be finished, for example, by electropolishing to a smooth finish. In some embodiments, about 0.0001 inch of the stent material can be removed by chemical milling and/or electropolishing to yield a stent.

Stent 20 can be of any desired size and shape (e.g., coronary stents, aortic stents, peripheral vascular stents, gastrointestinal stents, urology stents, and neurology stents). Depending on the application, stent 20 can have a diameter of between, for example, 1 mm to 46 mm. In certain embodiments, a coronary stent can have an expanded diameter of from about 2 mm to about 6 mm. In some embodiments, a peripheral stent can have an expanded diameter of from about 5 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm. A renal stent can have a diameter from about 8 mm to about 12 mm.

Stent 20 can be used, e.g., delivered and expanded, using a catheter delivery system. Catheter systems are described in, for example, Wang U.S. Pat. No. 5,195,969, Hamlin U.S. Pat. No. 5,270,086, and Raeder-Devens, U.S. Pat. No. 6,726,712, which are incorporated herein by reference. Stents and stent delivery are also exemplified by the Radius® or Symbiot® systems, available from Boston Scientific Scimed, Maple Grove, Minn.

While a number of embodiments have been described above, the invention is not so limited.

For example, the alloy compositions may further include oxygen, which is soluble in niobium and can have a potent effect on increasing yield strength. In some embodiments, the concentration of oxygen ranges from about 10 ppm to about 1,000 ppm, such as from about 50 ppm to about 300 ppm.

The alloy compositions can be used in other stent designs. The alloy compositions can be formed into wires or filaments that are subsequently knitted, woven, or crocheted to form tubular structure of a stent. Knitted and woven stents are described, for example, in Heath, U.S. Pat. No. 5,725,570; and Andersen, U.S. Pat. No. 5,366,504; Mayer, U.S. Pat. No. 5,800,511; Sandock, U.S. Pat. No. 5,800,519; and Wallsten, U.S. Pat. No. 4,655,771.

Furthermore, while stent 20 is shown having a tubular member made entirely of the alloy compositions described above, in other embodiments, the alloy compositions can be used to form one or more selected portions of a stent or other medical device. For example, a stent can be formed from a multilayered wire or filament, a multilayered sheet (e.g., rolled into a tube and joined at opposing edges), or a multilayered tube (e.g., by co-drawing multiple coaxial tubes), and one or more of the layers can include the alloy compositions. Referring to FIG. 2, a multilayered wire 40 includes a middle layer 42 having an Nb—Zr—W—Ta alloy composition as described herein, an outer layer 44, and an inner layer 46. Similarly, referring to FIG. 3, a multilayered stent 48 can include a middle layer 50 having an alloy composition as described herein, an outer layer 52, and an inner layer 54. In embodiments, middle layers 42 and 50 are capable of enhancing the MRI compatibility and radiopacity of wire 40. Outer and inner layers 44, 46, 52, and 54, which can have the same composition or different composition, can include any material suitable for medical device applications, such as stainless steel (e.g., 316L and 304L stainless steel), radiopacity enhanced steels (e.g., as described in US-2003-0018380-A1, US-2002-0144757-A1; and US-2003-0077200-A1), Nitinol (a nickel-titanium alloy), Elgiloy, L605 alloys, MP35N, Ti-6 Al-4V, Ti-50Ta, Ti-10Ir, Nb-1Zr, and Co-28Cr-6Mo. Other materials include elastic biocompatible metal such as a super-elastic or pseudo-elastic metal alloy, as described, for example, in Schetsky, L. McDonald, "Shape Memory Alloys", Encyclopedia of Chemical Technology (3rd ed.), John Wiley & Sons, 1982, vol. 20. pp. 726-736; and commonly assigned U.S. Ser. No. 10/346,487, filed Jan. 17, 2003. Alternatively or additionally to middle layers 42 and 50, the Nb—Zr—W—Ta alloy compositions can be included in other layers, such as the inner layer and/or the outer layer. Multilayered wires and tubes are described, for example, in Heath, U.S. Pat. No. 5,725,570.

In other embodiments, short fibers of the alloy compositions can be used to reinforce a matrix material, such as a polymeric material or another metallic material. Examples of medical devices having a matrix reinforced by fibers are described in Stinson, U.S. 2004-0044397.

Stent 20 can also be a part of a covered stent or a stent-graft. In other embodiments, stent 20 can include and/or be attached to a biocompatible, non-porous or semi-porous polymer matrix made of polytetrafluoroethylene (PTFE), expanded PTFE, polyethylene, urethane, or polypropylene.

Stent 20 can include a releasable therapeutic agent, drug, or a pharmaceutically active compound, such as described in U.S. Pat. No. 5,674,242, U.S. Ser. No. 09/895,415, filed Jul. 2, 2001, and U.S. Ser. No. 10/232,265, filed Aug. 30, 2002. The therapeutic agents, drugs, or pharmaceutically active compounds can include, for example, anti-thrombogenic agents, antioxidants, anti-inflammatory agents, anesthetic agents, anti-coagulants, and antibiotics. Alternatively or additionally, stent 20 can include one or more ceramic layers, such as niobium oxide and/or iridium oxide, as described in U.S. Pat. Nos. 6,387,121 and 6,245,104, by anodizing or otherwise oxidizing the stent. The ceramic layer(s) can enhance surface passivity, and in embodiments in which the layer(s) are porous, one or more drugs can be retained in the layer(s) for delivery after implantation.

In other embodiments, the structures and methods described herein can be used to make other medical devices, such as other types of endoprostheses, guidewires, hypotubes, catheters, distal protection devices, and abdominal aortic aneurysm repair devices. For example, the alloys can be used in filters such as removable thrombus filters described in Kim et al., U.S. Pat. No. 6,146,404; in intravascular filters such as those described in Daniel et al., U.S. Pat. No. 6,171,327; and vena cava filters such as those described in Soon et al., U.S. Pat. No. 6,342,062. The alloys can also be used in guidewires such as a Meier Steerable Guide Wire (for AAA stent procedure) and an ASAP Automated Biopsy System described in U.S. Pat. Nos. 4,958,625, 5,368,045, and 5,090,419.

The alloys can be used to form medical devices that benefit from having high strength to resist overloading and fracture, good corrosion resistance, and/or biocompatibility (e.g., capable of being implanted in a body for long periods (such as greater than ten years)). Examples of devices include internal and external fixation devices, hip stems, knee trays, dental prostheses, and needles.

The following examples are illustrative and not intended to be limiting.

Example 1

This example describes synthesis of an alloy with a nominal composition of Nb-28Ta-3.5W-1.3Zr.

The raw powder materials were weighed out to the desired proportions and melted in an arc melter (Materials Research Furnaces ABJ-900). The Zr powder was from Cerac; Z-1088, L/N X0027543, 99.8% pure; −140, +325 mesh. The Ta powder was from Cerac; T-1201, L/N X25522, 99.9% pure, −140, +325 mesh. The Nb powder was from Cerac; N-1096, L/N X22690, 99.8% pure, −140, +325 mesh. The W powder was from Cerac; T-1166, L/N X0027060, 99.5% pure, −100, +200 mesh. The powders were weighed out and mixed in three bottles as indicated in Table 3.

TABLE 3

| Charge No. | Nb powder, grams | Ta powder, grams | W powder, grams | Zr powder, grams |
|---|---|---|---|---|
| (1) | 31.8 | 13.5 | 2.0 | 0.6 |
| (2) | 31.9 | 13.4 | 1.4 | 0.7 |
| (3) | 31.1 | 13.4 | 1.5 | 0.6 |
| Total Mass | 94.8 | 40.3 | 4.9 | 1.9 |
| Weight % | 67 | 28 | 3.5 | 1.3 |

The powder from the charge bottles was poured into two ingot melt cavities in the arc melter. After the first melting operation, the two resultant ingots were combined in the largest elongated ingot cavity for the subsequent melting operations. A total of four melt operations were performed. The first was performed at 250 A to melt the powder. The second and third were performed at 400 amps to combine and repeatedly melt the ingots. The fourth was performed at 250 A to smoothen the surface to make machining easier. The resultant ingot weighed 141.3 grams.

The as-cast ingot was struck with a hammer ten times to see if the material had a level of ductility that would be suitable for machining and cold rolling. The ingot did not crack or fracture. The ingot was cut into three pieces in preparation for machining into rectangular bars (Table 4). One piece of the ingot (#3 below) was homogenized in a vacuum heat treat oven at 1200° C. for six hours prior to machining. This piece did not crack or fracture when struck with the hammer following the homogenization treatment.

TABLE 4

| Bar # | Length, inch | Width, inch | Thickness, inch |
|---|---|---|---|
| 1 | 1.50 | 0.44 | 0.20 |
| 2 | 1.45 | 0.45 | 0.20 |
| 3 | 1.47 | 0.49 | 0.20 |

The three machined bars were cold rolled to a total of 50% reduction in thickness and then annealed at 1200° C. in vacuum for 60 minutes and vacuum cooled in a vacuum heat treat furnace. The dimensions of the strips after cold rolling and heat treating were measured and found to be 2.3" long× 0.11" thick. The strip surfaces and edges were examined without magnification. Strips 1 and 2 had fine surface fissures. Strip 3 did not have any cracks or fissures.

The strips were cold rolled to a total of 50% reduction in thickness. The dimensions of the rolled strips are listed in Table 5. No cracks or fissures were observed on the strips.

TABLE 5

| Bar # | Length, inches | Width, inch | Thickness, inch |
|---|---|---|---|
| 1 | 3.72 | 0.65 | 0.055 |
| 2 | 4.00 | 0.58 | 0.056 |
| 3 | 4.18 | 0.60 | 0.055 |

The three strips were annealed in the vacuum heat treat furnace at 1200° C. for 30 minutes in vacuum and vacuum cooled. The purpose of this heat treatment was to recrystallize the cold worked microstructure and to soften the material for further cold rolling. The three strips were cold rolled to the following dimensions (Table 6).

TABLE 6

| Bar # | Length, inches | Width, inches | Thickness, inches |
|---|---|---|---|
| 1 | 7.0 | 0.66 | 0.027 |
| 2 | 7.8 | 0.59 | 0.028 |
| 3 | 8.0 | 0.61 | 0.027 |

The three strips were annealed in the vacuum heat treat furnace at 1200° C. for 30 minutes in vacuum and were vacuum cooled.

The three strips were then subjected to tensile specimen machining and testing. Included in the testing for comparison was a strip of Nb-50Ta alloy that was made with the arc melter and laboratory rolling mill (Sample X). Tensile data from commercially produced annealed Nb-50Ta strip (Heraeus) was included to allow comparison of laboratory arc melted material to commercially produced material. The 0.020" thick strip was machined into flat specimens similar to ASTM E8 FIG. 1 (0.125 inch width×0.02 inch thick×0.67 inch gage length). Testing was performed with a 0.5" extensometer gage length. The test specimen strain rate through 0.2% offset yield was 0.005 in./in./minute, and the crosshead extension rate was 0.02 inch/minute from yield to failure. Testing was conducted at room temperature.

TABLE 7

| Sample | Material: | Modulus (E), $10^6$ psi | UTS, ksi | 0.2% YS, ksi | Elongation, (%) from gage marks |
|---|---|---|---|---|---|
| Heraeus | Commercial Nb—50Ta | 19.9 | 47.1 | 35.1 | 23 |
| Sample X | Laboratory Nb—50Ta | 18.6 | 66.0 | 53.5 | 20 |
| Average of Samples #1-3 | Laboratory NbTaWZr | 18.7 | 69.0 | 50.8 | 17 |

The average tensile strength, yield strength, % elongation, and modulus of the arc melted, rolled, and annealed Nb—Ta—W—Zr alloy strips was similar to that of the Nb-50Ta alloy made in a similar way. The arc melted materials had higher strength and lower elongation that the Hereaus Nb-50Ta strip, and this is hypothesized to be attributed to higher oxygen concentration in the arc melted material relative to the commercially processed material.

In particular, the tensile properties of the arc melted Nb-28Ta-3.5W-1.3Zr alloy strip were similar to the arc melted Nb-50Ta alloy. This suggests that the solid solution strengthening from the Ta in Nb can be accomplished by tungsten and zirconium additions instead of only Ta. In some cases, Nb-50Ta may be too highly radiopaque in stent wall thicknesses, and the Nb-28Ta-3.5W-1.3Zr alloy may provide a more desirable level of radiopacity because the tantalum concentration is lower. At the same time, the Nb-28Ta-3.5W-1.3Zr alloy has a good modulus and yield strength (e.g., relative to Nb-1Zr alloy, which may have a yield strength about 10 ksi less).

Example 2

An ingot of the alloy was produced by vacuum arc remelting (VAR) of elemental raw materials by MetalWerks (Aliquippa, Pa.). In particular, Ta, Nb, and Zr plate pieces, along with a W sheet, were welded in a vacuum to form an electrode. The electrode was melted one time in a VAR furnace to make the ingot. The composition for the ingot as determined is shown in Table 8. The ingot was 2.425" in diameter, 6" long, and weighed about 11.1 pounds.

TABLE 8

| Ingot Composition | |
|---|---|
| Element | Weight Percent |
| Tantalum (Ta) | 30.6 |
| Tungsten (W) | 3.37 |
| Zirconium (Zr) | 1.36 |
| Oxygen (O) | 0.013 |
| Nitrogen (N) | 0.010 |
| Carbon (C) | 0.0050 |
| Hydrogen (H) | 0.0006 |
| Molybdenum (Mo) | 0.010 |
| Titanium (Ti) | <0.001 |
| Silicon (Si) | 0.003 |
| Iron (Fe) | 0.01 |
| Nickel (Ni) | 0.016 |
| Hafnium (Hf) | Not tested |
| Niobium (Nb) | balance |

The cylindrical ingot was axially drilled to produce a hollow cylinder (thick tube). The hollow cylinder was extruded to reduce diameter, increase length, and convert the as-cast microstructure to a wrought microstructure. The extrusion was vacuum annealed (2000-2100F for 2 hours) and pilgered to produce feedstock for tube mandrel drawing. Extrusion, pilgering, and mandrel drawing were performed by Noble-Met Inc. (Salem, Va.).

Two pilgered tubes were mandrel drawn to 0.072" OD×0.004" ID tubing. Standard commercial processing was utilized and included intermediate annealing steps. Vacuum annealing for two hours at 2050° F. produced a partially recrystallized structure, and two hours at 2100° F. produced mostly recrystallized structure. Twelve tensile tests were performed on the tubing in the 2100° F. annealed condition. Test speed was 0.02 inches/minute through yield and 0.20 inches/minute from thereon to failure. The results are listed in Table 9. The microstructure of the 2100 F annealed tubing consisted of fine equiaxed grains. The ASTM E112 average grain size number G was determined by the comparison method using Plate IV to be 9.6.

TABLE 9

Tensile results for tubing in 2100° F. annealed condition

| Test Specimen: | Modulus (E), mpsi | 0.2% offset YS, ksi | UTS, ksi | % elongation |
|---|---|---|---|---|
| Mean | 17.5 | 43.0 | 62.2 | 25.9 |
| Std Dev | 0.6 | 1.8 | 0.7 | 1.8 |

All publications, references, applications, and patents referred to herein are incorporated by reference in their entirety.

Other embodiments are within the claims.

What is claimed is:

1. A stent comprising a tubular member comprising a plurality of bands and a plurality of connectors that extend between and connect adjacent bands, the tubular member comprising an alloy comprising:
   about 0.1% by weight to about 40% by weight of tantalum;
   about 0.1% by weight to about 25% by weight of tungsten plus zirconium;
   about 41% by weight to about 79% by weight of niobium; and
   about 0.5% by weight to about 20% by weight of titanium.

2. The stent of claim 1, wherein the alloy comprises from about 20% to about 40% by weight of tantalum.

3. The stent of claim 1, wherein the alloy comprises from about 0.5% to about 9% by weight of tungsten.

4. The stent of claim 1, wherein the alloy comprises from about 0.5% to about 10% by weight of zirconium.

5. The stent of claim 1, wherein the alloy comprises from about 20% to about 40% by weight of tantalum, from about 0.5% to about 9% by weight of tungsten, and from about 0.5% to about 10% by weight of zirconium.

6. The stent of claim 1, wherein the alloy further comprises an element selected from the group consisting of molybdenum, rhenium, iridium, and hafnium.

7. The stent of claim 6, wherein the alloy comprises about 0.5% by weight to about 8% by weight of iridium.

8. The stent of claim 6, wherein the alloy comprises about 0.5% by weight to about 5% by weight of rhenium plus molybdenum.

9. The stent of claim 6, wherein the alloy comprises about 1% by weight to about 12% by weight of hafnium.

10. The stent of claim 9, wherein the alloy comprises about 7% by weight to about 12% by weight of hafnium.

11. The stent of claim 1, wherein the alloy has an elastic modulus of from about 10 million psi to about 30 million psi, a percent elongation of from about 10% to about 40% to fracture, and a yield strength of from about 20 thousand psi to about 60 thousand psi.

12. The stent of claim 1, wherein the tubular member is a multilayered structure, wherein one layer of the multilayered structure comprises the alloy.

13. A stent comprising a tubular member comprising a plurality of bands and a plurality of connectors that extend between and connect adjacent bands, the tubular member comprising an alloy comprising:
   about 0.1% by weight to about 40% by weight of tantalum;
   about 0.1% by weight to about 25% by weight of tungsten plus zirconium;
   about 41% by weight to about 79% by weight of niobium; and
   about 0.5% by weight to about 8% by weight of iridium.

14. The stent of claim 13, wherein the alloy comprises from about 20% to about 40% by weight of tantalum, from about 0.5% to about 9% by weight of tungsten, and from about 0.5% to about 10% by weight of zirconium.

15. A stent, comprising a tubular member comprising a plurality of bands and a plurality of connectors that extend between and connect adjacent bands, the tubular member comprising an alloy comprising:
   about 0.1% by weight to about 40% by weight of tantalum;
   about 0.1% by weight to about 25% by weight of tungsten plus zirconium;
   about 41% by weight to about 79% by weight of niobium; and
   10 ppm to about 1,000 ppm oxygen.

16. The stent of claim 15, wherein the alloy comprises from about 20% to about 40% by weight of tantalum, from about 0.5% to about 9% by weight of tungsten, and from about 0.5% to about 10% by weight of zirconium.

17. The stent of claim 15, wherein the alloy comprises about 0.5% by weight to about 8% by weight of iridium.

18. The stent of claim 15, wherein the alloy comprises about 0.5% by weight to about 5% by weight of rhenium plus molybdenum.

19. The stent of claim 15, wherein the alloy comprises about 1% by weight to about 12% by weight of hafnium.

20. The stent of claim 15, wherein the alloy comprises about 0.5% by weight to about 20% by weight of titanium.

* * * * *